(12) United States Patent
Güller et al.

(10) Patent No.: US 6,268,499 B1
(45) Date of Patent: Jul. 31, 2001

(54) PROCESS AND INTERMEDIATES FOR PREPARATION OF SUBSTITUTED PIPERIDINE-EPOXIDES

(75) Inventors: Rolf Güller, Herznach; Bruno Lohri, Reinach; Rudolf Schmid, Basel, all of (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/351,643

(22) Filed: Jul. 13, 1999

(30) Foreign Application Priority Data

Aug. 10, 1998 (EP) .................................. 98114975

(51) Int. Cl.⁷ ................................. C07D 491/08
(52) U.S. Cl. ............................................. 546/115
(58) Field of Search ............................. 546/115

(56) References Cited

U.S. PATENT DOCUMENTS 3,954,876  5/1976  Vofsi et al. ................... 568/320

FOREIGN PATENT DOCUMENTS

| 2600557 | * 9/1976 | (DE) . |
| 0 979 819 | 2/2000 | (EP) . |
| WO 97/09311 | 3/1997 | (WO) . |

OTHER PUBLICATIONS

Diez et al. "Preparation of new chiral piperidine epoxides" CA 116:106133, 1991.*
J. Org. Chem. 1971, vol. 36(17) Sundberg, R.J., et al. pp. 2471–2480.
Chem. Pharm. Bull. 1980 vol. 28(5), Nagai, Y, et al. pp. 1387–1393.
Synth. Commun. 1981, vol. 11(8) pp. 615–625, Hershenson, F.M. et al.
Tetrahedron Lett. 1996 vol. 37(47), Rousselet G., et al. pp. 8479–8500.
Houben–Weyl, Methods of Organic Chemistry (Theime, 1952, pp. vol. E21 pp. 81–91).
S.L. Buchwald et al., J. Org. Chem. 1997, vol. 62 pp. 1568–1569.

* cited by examiner

*Primary Examiner*—Ceila Chang
(74) *Attorney, Agent, or Firm*—George W. Johnston; Patricia S. Rocha-Tramaloni; Robert A. Silverman

(57) ABSTRACT

The present invention concerns intermediates useful in and a process for the preparation of a compound of formula 1 or a salt thereof

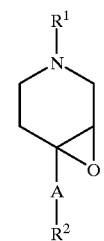

comprising epoxidation of a compound of formula 2 or a salt thereof

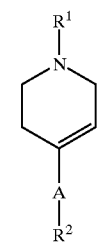

wherein A, $R^1$ and $R^2$ are as herein defined. These compounds are useful in the synthesis of renin inhibitors.

21 Claims, No Drawings

PROCESS AND INTERMEDIATES FOR PREPARATION OF SUBSTITUTED PIPERIDINE-EPOXIDES

SUMMARY OF THE INVENTION

The invention relates to a intermediates useful in a process for the preparation of substituted piperidine-epoxides. More particularly, the invention relates to the preparation of compounds of the formula 1

and salts thereof, wherein

| A | is arylene; |
|---|---|
| $R^1$ | is $-C^*R^3R^4R^5$; |
| $R^2$ | is -O-alkyl, -O-cycloalkyl, -O-alkenyl, -O-aryl, -O-aralkyl, -O-aralkoxyalkyl, -O-alkylsulfonyl, -O-arylsulfonyl, chlorine, bromine or iodine; |
| $R^3$ | is hydrogen; |
| $R^4$ | is aryl; |
| $R^5$ | is alkyl, cycloalkyl, aryl, alkoxyalkyl or hydroxyalkyl; |
| and $C^*$ | is an asymmetric carbon atom. |

The invention also relates to compounds of formula 1, which are useful as chiral building blocks in the preparation of renin inhibitors, especially trisubstituted renin inhibitors as is disclosed in WO 97/09311 e.g. (3R,4S,5S)-4-[4-(3-benzyloxy-propoxy)-phenyl [-5-ethoxy-3-(naphthalen-2-ylmethoxy)-piperidine.

BACKGROUND OF THE INVENTION

The syntheses of optically active renin inhibitors via resolution of racemates as disclosed in WO 97/09311 results in a considerable loss of product. The present invention provides a novel process which avoids the disadvantages of this process.

DETAILED DESCRIPTION OF THE INVENTION

According to the present invention, compounds of formula 1 above and their salts can be prepared by a process comprising:

a) epoxidation of a compound of formula 2 or a salt thereof

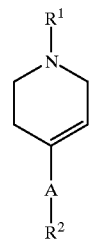

wherein
$R^1$, $R^2$ and A are defined as above.

In another embodiment of the present invention, step a) above may be optionally followed by isolation of the desired stereoisomer.

The term "alkyl" means alone or in combination a branched or unbranched alkyl group containing 1 to 8 carbon atoms, preferred 1 to 6 carbon atoms. Examples for branched or unbranched $C_1-C_8$ alkyl groups are methyl, ethyl, propyl, isopropyl, butyl, isobutyl, tert-butyl, the isomeric pentyls, the isomeric hexyls, the isomeric heptyls, the isomeric octyls and preferred ethyl, n-propyl, and isopropyl and particularly preferred methyl.

The term "cycloalkyl" means alone or in combination a cycloalkyl cycle with 3 to 8 carbon atoms and preferred a cycloalkyl cycle with 3 to 6 carbon atoms. Examples for $C_3-C_8$ cycloalkyl are cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl and cycloheptyl.

The term "alkenyl" means alkenyl groups of 2 to 8 carbon atoms. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-ethyl-2-butenyl, and the like. Preferred is allyl.

The term "aryl" means alone or in combination a phenyl or a naphthyl group which can be substituted by one or several substituents chosen from alkyl, cycloalkyl, alkoxy, halogen, carboxy, alkoxycarbonyl, hydroxy, amino, nitro, trifluoromethyl and the like. Examples for aryl are phenyl, tolyl, methoxyphenyl, fluorophenyl, chlorophenyl, hydroxyphenyl, trifluoromethylphenyl, 1-naphthyl and 2-naphthyl.

The term "arylene" means alone or in combination a phenylene or a naphthylene group which optionally can be substituted by one or several substituents chosen from alkyl, cycloalkyl, halogen, nitro, alkoxy, hydroxy, amino, preferably alkyl, halogen and nitro. Examples for arylene are ortho-phenylene, meta-phenylene, para-phenylene, the tolylenes, methoxyphenylenes, fluorophenylenes, chlorophenylenes and naphthylenes. Preferred are phenylene, wherein the substituents of the phenylene which are defined by formula 1 are placed ortho, meta or preferred para to one another and wherein one or several additional substituents chosen from alkyl, halogen and nitro can be present at the arylene cyclus. Especially preferred substituents are methyl, chloro and nitro. Particularly preferred is unsubstituted phenylene and especially unsubstituted para phenylene.

The term "alkoxy" means alone or in combination the group 13 O-alkyl, wherein alkyl is defined as before. Examples are ethoxy, n-propyloxy, and iso-propyloxy. Preferred is methoxy.

The term "alkoxyalkyl" means alone or in combination an alkyl group, wherein a hydrogen is substituted by an alkoxy group. Examples are methoxymethyl, ethoxymethyl and 2-methoxyethyl. Particularly preferred is methoxymethyl.

The term "hydroxyalkyl" means alone or in combination an alkyl group, wherein a hydrogen is substituted by an hydroxy group. Examples are hydroxymethyl, 1-hydroxyethyl and 2-hydroxyethyl. Preferred is hydroxymethyl.

The term "aralkyl" means alone or in combination an alkyl group, wherein a hydrogen is substituted by an aryl group. A preferred example is benzyl.

The term "aralkoxyalkyl" means alone or in combination an alkyl group, wherein a hydrogen is substituted by an alkoxy group in which a hydrogen is substituted by an aryl group. A preferred example for aralkoxyalkyl is 3-(2-methoxy-benzyloxy)-propyl.

The term "alkylsulfonyl" means alone or in combination a sulfonyl group which is substituted by an alkyl group. The alkyl group can be substituted by halogen. Preferred examples are methylsulfonyl and trifluoromethylsulfonyl.

The term "arylsulfonyl" means alone or in combination a sulfonyl group which is substituted by an aryl group. Preferred is the tosyl group.

The term "salts" means compounds which are formed by reaction of compounds of formula 1 with inorganic acids such as hydrochloric acid, hydrobromic acid, sulfuric acid, nitric acid, phosphoric acid, and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. The term salts includes solvates and particularly hydrates of such salts.

The term "halogen" means fluorine, chlorine, bromine, iodine, preferably chlorine and bromine. Most preferred is chlorine.

The term "anion" means an atom, a group of atoms or a molecule with negative charge. This charge can be a single or a multiple charge. Examples of anions are the halogen anions, $SO_4^{2-}$, $PO_4^{3-}$. Particularly preferred is the Cl⁻ anion.

The term "asymmetric carbon atom (C*)" means a carbon atom with four different substituents. According to the Cahn-Ingold-Prelog-Convention, the asymmetric carbon atom have "R " or "S " configuration. A preferred example for an asymmetric carbon atom (C*) is shown in the formula

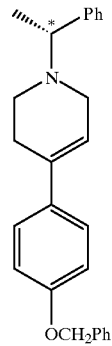

wherein the asymmetric carbon atom C* is of the R configuration.

The term "—O—" in groups such as —O-alkyl, —O-cycloalkyl, —O-alkenyl, —O-aryl, —O-benzyl, —O-aralkoxyalkyl, —O-alkylsulfonyl, —O-arylsulfonyl, means an oxygen with a free valence. For example —O-alkyl means alkoxy and —O-cycloalkyl means cycloalkoxy.

In a preferred embodiment, the above process is used to prepare compounds of the formula 1 wherein $R^5$ is alkyl or cycloalkyl and $R^1$, $R^2$ and A are defined as above.

Also preferred is a process according to the present invention, wherein $R^4$ is unsubstituted phenyl or substituted phenyl and, wherein the substituents of phenyl are independently selected from one or more of alkyl, halogen or nitro, preferably methyl or chloro. In a particularly preferred embodiment of the above process $R^4$ is unsubstituted phenyl and $R^1$, $R^2$ and A are as defined above.

Particularly preferred is the above process above, wherein $R^4$ is phenyl, particularly unsubstituted phenyl, and $R^5$ is methyl and $R^1$, $R^2$ and A are as otherwise defined above.

In another preferred embodiment of the present invention, A is substituted or unsubstituted ortho, meta or para phenylene. When substituted, the substituents on the phenylene are placed ortho, meta or para to one another. The para position is preferred. The substituted phenylene has one to four substituents chosen from alkyl, halogen and nitro. Most preferably, A is unsubstituted phenylene, and in particular unsubstituted para phenylene.

In another preferred embodiment of the present invention, $R^2$ is selected from —O-alkyl, —O-cycloalkyl, —O-aryl, or —O-aralkyl. Preferably $R^2$ is selected from —O-benzyl and —O-methyl. Particularly preferred $R^2$ is —O-benzyl.

Epoxidation of a compound of formula 2 may be effected by use of halogen or a halogen delivering agent such as N-bromine compounds. Preferably, the halogen or halogen delivering agent is selected from bromine, N-bromosuccinimide, dibromoisocyanurate and 1,3-dibromo-5,5-dimethylhydantoin. Particularly preferred is bromine.

The present invention is also directed to compounds of formula 1 wherein $R^1$, $R^2$ and A are defined as above, and to salts of these compounds. Preferred compounds of formula 1 include (1R, 6R)-6-(4-benzyloxy-phenyl)-3-[(R)-1-phenyl-ethyl]-7-oxa-3-aza-bicyclo [4.1.0] heptane.

Compounds of formula 2 above and their salts are new and also form part of the present invention. Preferred compounds of formula 2 include (R)-4-(4-benzyloxy-phenyl)-1-(1-phenyl-ethyl)-1,2,3,6-tetrahydro-pyridine and salts thereof.

Compounds of formula 2 may be obtained by reacting a compound of formula 3 or 4

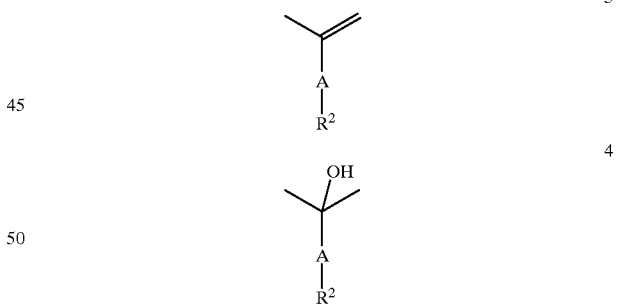

with a compound of the formula $R^1$-$NH_2$ or a salt thereof, wherein $R^1$, $R^2$ and A have the same meaning as given above. Preferably, this reaction is effected in the presence of formaldehyde (a reactant) or a compound which forms formaldehyde during the above reaction ("chemical equivalent" thereof).

Another preferred aspect of the present invention is the isolation of the desired stereoisomer of a compound of formula 1 or a salt thereof, preferably by crystallisation. Particularly preferred is the crystallisation of the free compound of formula 1. Crystallization of compounds of formula I or a salt thereof is accomplished by methods known to those skilled in the art, preferably in the presence of ethyl acetate.

In another embodiment of the present invention, to open the epoxide the above process is followed by a reaction with a metal alcoholate. A particularly preferred embodiment is the reaction of a compound of formula 1 or a salt thereof, preferably the desired stereoisomer of a compound of formula 1 or a salt thereof, with potassium t-butoxide, aluminium isopropoxide, titanium (IV) t-butoxide, with a lithium amide such as lithium diisopropylamide or with an organolithium compound such as phenyllithium, sec-butyllithium or methyllithium, to form a compound of formula 5

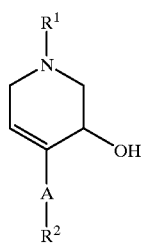

5 or a salt thereof. Most preferred is the reaction of a compound of the formula 1 or a salt thereof, preferably the desired stereoisomer of a compound of the formula 1 or a salt thereof, with phenyllithium reacts.

The invention also relates to the transformation of compounds of the formula 1 or a salt thereof to renin inhibitors, especially trisubstituted renin inhibitors such as (3R,4S,5S)-4-[4-(3-benzyloxy-propoxy)-phenyl]-5-ethoxy-3-(naphthalen-2-ylmethoxy)-piperidine. Preferably, this transformation is effected by (1) reaction of a compound of formula 1 or a salt thereof, or the desired stereoisomer of a compound of formula 1 or a salt thereof, with phenyllithium, (2) alkylation of the 3-hydroxy function of the product of step (1), (3) hydroboration of the resulting ether compound formed in step (2) and subsequent basic oxidative working-up of the resulting intermediate carboborane to transform the carboborane into a secondary alcohol, (4) reorganization of protective groups, (5) removal of the N-phenylethyl and the O-benzyl function and re-introduction of a N-Boc protective group, (6) selective functionalization of the phenolic function, (7) alkylation of the secondary hydroxy function of the piperidine ring and (8) removal of the Boc-protective group. (1R,6R)-6-(4-benzyloxy-phenyl)-3-[(R)-1-phenyl-ethyl]-7-oxa-3-aza-bicyclo[4.1.0] heptane is converted to (3R,4S,5S)-4-[4-(3-benzyloxy-propoxy)-phenyl]-5-ethoxy-3-(naphthalen-2-ylmethoxy)-piperidine by the following procedure:

a) reacting (1R, 6R)-6-(4-benzyloxy-phenyl)-3-[(R)-1-phenyl-ethyl]-7-oxa-3-aza-bicyclo [4.1.0] heptane with phenyllithium to yield (3S)-4-(4-benzyloxy-phenyl)-1-[(1R)-phenyl-ethyl]-1,2,3,6-tetrahydro-pyridin-3-ol;

b) reacting the product of step a) with sodium hydride and ethyl iodide to yield (3S)-4-(4-benzyloxy-phenyl)-3-ethoxy-1- [(1R)-phenyl-ethyl]-1,2,3,6-tetrahydro-pyridine;

c) hydroborating the product of step b) with sodium borohydride and boron trifluoride etherate followed by reacting the hydrobonated product with potassium hydroxide and hydrogen peroxide to yield (2R,4R,5S)-(4-benzyloxy-phenyl)-5-ethoxy-1-[(1R)-phenyl-ethyl]-piperidin-3-ol);

d) hydrogenolysis of the product of step c) to yield (3R,4R,5S)-5-ethoxy-4-(4-hydroxy-phenyl)-piperidin-3-ol;

e) reacting the product of step d) with di-tert-butyldicarbonate and sodium hydrogencarbonate followed by addition of NaOH to yield (3R,4R,5S)-5-ethoxy-3-hydroxy-4-(4-hydroxy-phenyl)-piperidine-1-carboxylic acid tert-butylester;

f) treating the product of step e) with 3-bromo-propoxymethyl-benzene and potassium carbonate to yield (3R,4R,5S)-4-[4-(3-benzyloxy-propoxy)-phenyl]-5-ethoxy-3-hydroxy-piperidine-1-carboxylic acid tert-butylester;

g) reacting the product of step f) with 2-bromomethyl-naphthalene and sodium hydride to yield (3R,4S,5S)-4-[4-(3-benzyloxy-propoxy)-phenyl]-5-ethoxy-3-(naphthalen-2-ylmethoxy)-piperidine-1-carboxylic acid tert-butylester;

h) reacting the product of step g) with hydrochloric acid to yield (3R,4S,5S)-4-[4-(3-benzyloxy-propoxy)-phenyl]-5-ethoxy-3-(naphthalen-2-ylmethoxy)-piperidine.

Furthermore, compounds of formula 6 and their salts are also a part of the present invention:

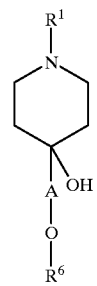

6 wherein $R^1$ and A are defined as above and $R^6$ is alkyl, cycloalkyl, alkenyl, aryl, aralkyl, aralkoxyalkyl, alkylsulfonyl or arylsulfonyl.

Particularly preferred compounds of formula 6 include (R)-4-(4-benzyloxy-phenyl)-1-(1-phenyl-ethyl) piperidin-4-ol and salts thereof.

Moreover, compounds of formula 5 and their salts are part of the present invention. Prefered compounds of formula 5 include (3S)-4-(4-benzyloxy-phenyl)-1-[(1R)-phenyl-ethyl]-1,2,3,6-tetrahydro-pyridin-3-ol.

The invention also relates to the use of a compound of formula 1 in the preparation of renin inhibitors, preferably in the preparation of (3R,4S,5S)-4-[4-(3-benzyloxy-propoxy)-phenyl]-5-ethoxy-3-(naphthalen-2-ylmethoxy)-piperidine, as described above.

Furthermore, the invention also relates to compounds as obtained by the above described processes.

More specifically, the process of the invention may be described as follows: Epoxidation of a compound of formula 2 or a salt thereof and optionally isolation of the desired stereoisomer:

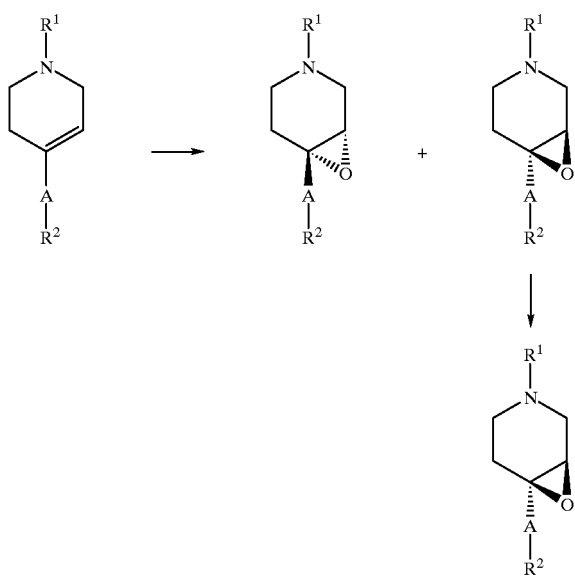

wherein $R^1$, $R^2$ and A are defined as before.

A compound of the formula 2 can be reacted with compounds which are known for use in epoxidation reactions. Examples for such compounds are halogens and organic bromo-compounds such as N-bromosuccinimide, dibromoisocyanurate and 1,3-dibromo-5,5 -dimethylhydantoin. Preferred is bromine, especially in the presence of an acid, preferably HBr and chemical equivalents thereof.

Inert solvents taken alone or in combination can be used, particularly, solvents which are known for their utilisation in epoxidation reactions. Examples of such solvent are straight or cyclic ethers dimethylether, diethylether, tetrahydrofuran and monoglyme or diglyme alone or in such a combination that a sufficient miscibility with water is given. A preferred solvent is dioxane.

Preferred is the above reaction in the presence of an acid. Examples of such acids are optically active or inactive acids such as the hydrohalic acids, sulfonic acids and $H_2SO_4$. Particularly preferred is HBr. In general the above reaction can be performed in a wide pH range. Preferred is a pH range from about 1 to 4 and particularly preferred is a pH range from about 1.5 to 3.

A temperature range of from about −20° C. to the boiling point of the solvent is suitable for the reaction of the present invention. The preferred temperature range is between about −20° C. to about 20° C. preferably from about 0° C. to about 5° C.

In a preferred aspect, the above reaction is followed by addition of a base such as NaOH, KOH, or a nitrogen-base such as triethylamine. Preferred is the use of NaOH or KOH. The temperature range for the addition of the base is between about −20° C. and about the boiling point of the solvent. A preferred temperature range for the addition of the base is from about between −20° C. to about 20° C., most preferably from about 0° C. to about 5° C. In case the epoxidising agent reacts with a compound of the formula 2 without addition of an acid, the epoxide can be obtained without using a base.

According to the above process compounds of formula 1 may be formed as a mixture of stereoisomers, preferably as a mixture of diastereomers. It is also possible that only one of the diastereomers is formed by the above process. In a preferred embodiment of the described process, only one of the diastereomers is formed.

In a preferred embodiment of the invention epoxidation of (R)-4-(4-benzyloxy-phenyl)-1-(1-phenyl-ethyl)-1,2,3,6-tetrahydro-pyridine yields a mixture of (1R, 6R)-6-(4-benzyloxy-phenyl)-3-[(R)-1-phenyl-ethyl]-7-oxa-3-aza-bicyclo [4.1.0] heptane and of (1S, 6S)-6-(4-benzyloxy-phenyl)-3-((R1)-1-phenyl-ethyl]-7-oxa-3-aza-bicyclo [4.1.0] heptane Optionally, the desired stereoisomer, especially the desired diastereomer, can be isolated by methods known in the art such as crystallisation, chromatography or distillation, preferably crystallisation or chromatogaphy. These methods also include the formation of salts or derivatives of compounds of the formula 1 followed by separation of these salts or derivatives by crystallisation, chromatography or distillation. These methods, for the separation of diastereoisomers are well known in the art and are for example described in Houben-Weyl, Methods of Organic Chemistry (Theime, 1952, pp. Vol. E21, p. 81, 91).

Preferred solvents taken alone or in combination which can be used for the crystallisation of compounds of formula 1 and salts thereof are protic or aprotic solvents that do not react with compounds of formula 1. Examples of such solvents are alcohols such as ethanol, isopropanol or methanol, esters such as ethyl acetate, ethers such as diethyl ether or a diisopropyl ether. The solvents may be used alone or in a suitable combination or also in combination with an appropriate amount of a hydrocarbon such as pentane or hexane. Particularly preferred solvents include ethyl acetate, especially used in combination with diethyl ether.

A preferred method of isolation of the desired diastereomer is by crystallisation of a free compound of formula 1, particularly in ethyl acetate in combination with diethyl ether.

After the formation of compounds of formula 1 the epoxide is opened by reaction with a metal alcoholate such as potassium t-butoxide, aluminium isopropoxide, titanium (IV) t-butoxide, with a lithium amide such as lithium diisopropylamide or with an organolithium compound such as phenyllithium, sec-butyllithium or methyllithium to give a compound of formula 5 or a salt thereof.

In a preferred embodiment of the above process, of a compound of formula 1 or a salt thereof, is reacted with phenyllithium to give a compound of formula 5. Particularly preferred is reacting the desired stereoisomer of a compound of the formula 1 with phenyllithium. Preferred solvents for this reaction, taken alone or in combination, are ethers such as tetrahydrofuran, diethyl ether, or tert-butyl methyl ether, aromatic hydrocarbons such as toluene or chlorobenzene or pyridine. In the case of phenyllithium as the reagent, tert-butyl methyl ether is a particularly preferred solvent.

The opening of the epoxide can be performed in a temperature range from about −40° C. up to the boiling of the solvent. The preferred temperature range is from about −25° C. up to about 0° C. Most preferred is a temperature of about −15° C.

A compound of formula 1 wherein $R^2$ is chlorine, bromine or iodine is converted to the corresponding allylic alcohol of formula 5 by using a reagent such as aluminium isopropoxide. The halogen substituent can be replaced by an oxygen substituent, a carbon substituent or a nitrogen substituent by using an appropriate oxidant, by using conditions for transition metal catalyzed Heck or cross-coupling reactions or by using amination conditions with transition metal catalysis (S. L. Buchwald et al., J. Org. Chem. 1997, 62, 1568), respectively.

The resulting opened epoxide or allylic alcohol compound can then be used in the preparation of renin inhibitors as is disclosed in WO 97/09311 as follows: Alkylation of the 3-hydroxy function, for example of (3S)-4-(4-benzyloxy-phenyl)-1-[(1R)-phenyl-ethyl]-1,2,3,6-tetrahydro-pyridin-3-ol, can be performed in solvents as ethers like tetrahydrofuran and 1,2-dimethoxyethane, dimethylformamide or dimethylsulfoxide with aliphatic chlorides, bromides, iodides, tosylates or mesylates in the presence of a base like sodium hydride or potassium tert-butoxide. The alkylating agents used can either contain the whole substituent desired to be included or optionally can be suitably protected by functional groups which allow further structural modifications at a later stage of the synthesis. This substituent is represented by R' in formula 7 and 8.

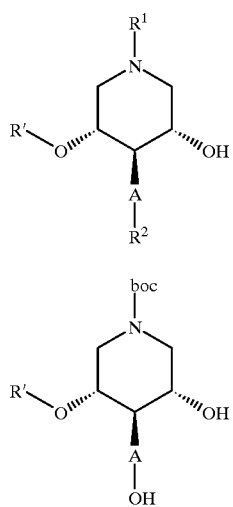

Hydroboration of the resulting alkylated compounds followed by subsequent basic oxidative working-up produces compounds of the formula 7, with high diastereoselectivity. The hydroboration can be effected according to known methods in an inert solvent such as an ether, for example 1,2-dimethoxyethane, at a temperature between about 0° C. and about 70° C., and with a diborane-containing or diborane-liberating reagent such as for example borane in tetrahydrofuran or a mixture of sodium borohydride and boron trifluoride diethyletherate. The resulting carboboranes which are formed as intermediates can be converted into secondary alcohols of formula 7 by reaction with a base, for example potassium hydroxide, and an oxidizing agent, for example hydrogen peroxide, at a temperature between about room temperature and about 120° C. Reorganization of protective groups, removal of the $R^1$ and $R^2$ groups from compounds of formula 7 and re-introduction of a N-protective group are effected by known methods: Hydrogenolysis with hydrogen in the presence of a palladium catalyst followed by introduction of the Boc group with di-tert-butyldicarbonate in dioxane/water converts compounds of formula 7 into a compound of formula 8, bearing a phenolic and an aliphatic OH-function which can be functionalized selectively.

Selective functionalization of the phenolic function in compounds of formula 8 can be performed with alkylation reactions using aliphatic or benzylic chlorides, bromides, iodides, tosylates or mesylates in the presence of a base like potassium carbonate in solvents such as an ether like tetrahydrofuran, or in dimethylformamide, dimethylsulfoxide, acetone, methyl-ethyl-ketone, or pyridine at temperatures between about 0° C. and about 140° C.

The alkylating agents used can either contain the whole substituent desired to be included or optionally can be suitably protected by functional groups which allow further structural modifications at a later stage of the synthesis. Functionalization at the secondary hydroxy function of the piperidine ring can then be performed in solvents as ethers like tetrahydrofuran or 1,2-dimethoxyethane, or in dimethylformamide or dimethylsulfoxide in the presence of a base like sodium hydride or potassium tert-butoxide and a suitable alkylating agent, preferentially an aryl methyl chloride, bromide, mesylate or tosylate at temperatures between about 0° C. and about 40° C. The alkylating agents used can either contain the whole substituent desired to be included or optionally can be suitably protected by functional groups which allow further structural modifications at a later stage of the synthesis. Further structural variations can comprise removal of protective functions followed by functionalizations of the liberated functional groups, for example etherification of a phenolic moiety. Final removal of the Boc-protective group can be performed in the presence of acids such as hydrochloric, hydrobromic, sulfuric, phosphoric, trifluoroacetic acid in a variety of solvents such as alcohols and alcohol/water mixtures, ethers and chlorinated hydrocarbons. The Boc-protective group can also be removed with anhydrous zinc bromide in inert solvents such as dichloromethane.

The compounds of formula 2 can be prepared as follows:

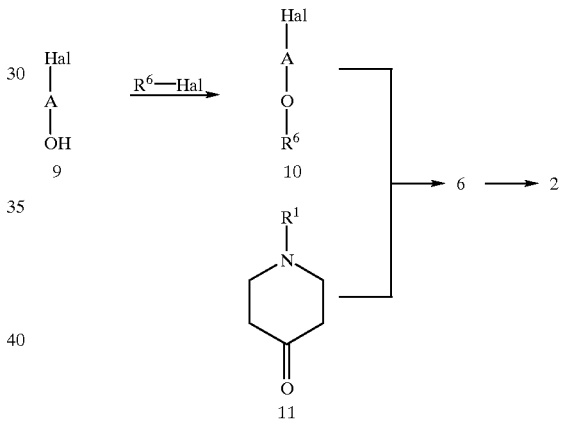

Compound 6 is reacted with an acid, e.g. oxalic acid dihydrate in an inert solvent to form a compound of formula 2. Compound 6 is formed by reacting a compound of formula in an inert solvent with n-butyllithium or a Grignard reagent to form an organometallic intermediate which is reacted with a compound of the formula 11. Compound 10 can be obtained by reacting a compound of formula 9 with a compound of the formula $R^6$-Hal in the presence of a base and preferably a catalyst such as NaI in an inert solvent. $R^6$ is alkyl, cycloalkyl, alkenyl, aryl, aralkyl, aralkoxyalkyl, alkylsulfonyl or arylsulfonyl. Compound 11 can be obtained by the reaction of $R^1$—$NH_2$ with 1-ethyl-1-methyl-4-oxo-piperidinium-iodide in the present of a base. 1-Ethyl-1-methyl-4-oxo-piperidinium-iodide can be obtained by the reaction of 1-ethyl-4-piperidone with methyl iodide in an inert solvent.

Alternatively, a compound of formula 2 can be obtained by the reaction of an ammonium salt having the formula $R^1$—$NH_3^+X^-$ with formaldehyde and a compound of formula 3. Compounds of formula 3 can be obtained by a reaction of methyltriphenylphosphonium-bromide, potassium tert-butoxide and a compound of formula 12 in an inert solvent.

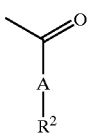

Alternatively, compounds of formula 2 can be prepared by the reaction of an ammonium salt of the formula $R^1$—$NH_3^+$ $X^-$ with formaldehyde and with a compound of formula 4. Compounds of formula 4 can be prepared by the reaction of an organometallic compound containing a methyl group attached to the metal as in methylmagnesium bromide or methyllithium, with compound 9. Compounds of formula 4 wherein $R^2$ is chlorine, bromine or iodine can be prepared via oxidation of a halocumene (for example described in U.S. Pat. No. 3954876 or DE 2302751).

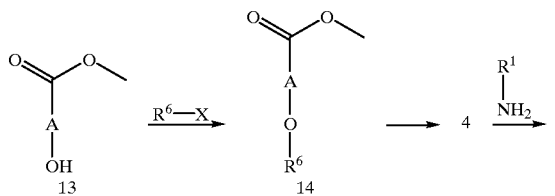

Alternatively, compounds of formula 2 can be prepared by reacting a salt of the formula $R^1$—$NH_3X$ with formaldehyde and a compound of formula 4. Preferably, $R^1$—$NH_3X$ is generated in the reaction mixture from a compound $R^1$—$NH_2$ using the appropriate amount of a suitable acid HX. Furthermore, a compound of formula 4 can be obtained by the reaction of a compound of formula 14 with an appropriate organometallic compound. Compound 14 can be prepared by reacting a compound of formula 13 with $R^6$—X in the presence of a base in an inert solvent. $R^6$ has the meaning given above.

The following preparations and examples illustrate preferred embodiments of the present invention but are not intended to limit the scope of the invention.

EXAMPLES

Example 1

Preparation of Product

Preparation of (1R, 6R)-6-(4-benzyloxy-phenyl)-3-[(R)-1-phenyl-ethyl]-7-oxa-3-aza-bicyclo [4.1.0] heptane 44.3 g of (R)-4-(4-Benzyloxy-phenyl)-1-(1-phenyl-ethyl)-1,2,3,6 tetrahydropyridine (120 mmol) was suspended in 440 mL of dioxane at room temperature. Under stirring 40.4 g of 48% aqueous hydrogen bromide (240 mmol) was added at 15–20° C. within 5 minutes, followed by 24 mL of water. At the same temperature, the pH of the mixture was adjusted to pH 2 using 65 mL of 2 N NaOH. The slightly turbid solution was cooled to 2–3° C, and 21.2 g of bromine (133 mmol) was continuously added over 1.5 hours from a syringe pump via a teflon cannula. After the bromine addition, stirring at 2–3° C. was continued for another 1.5 hours. At this point, all starting material had reacted. At 0° C., 160 mL of 4 N NaOH (640 mmol) was added over 30 minutes and stirring was continued. After 2 hours the intermediate had completely reacted to the final product. The reaction mixture was extracted using a mixture of 500 mL of ethyl acetate and 200 mL of 20% aq. sodium chloride. The aqueous phase was separated and extracted with 1 portion of 300 mL of ethyl acetate. The organic phases were washed with 300 ml of 20% aq. sodium chloride, combined, dried (MgSO$_4$) and evaporated under reduced pressure to give 51.3 g crude product as a brown oil. The crude product was taken up in 50 mL of ethyl acetate. Immediately after dissolution crystals started to separate. 50 mL of diethyl ether was added and the suspension was cooled to 0° C. A second portion of 25 mL of diethyl ether was added and the suspension was stirred for another 1 hour at 0° C. The crystals were collected on a filter funnel and washed with a portion of cold diethyl ether. The product was then dried for 2 hours at 26 mbar/45° C. There was obtained 23.5 g of (1R, 6R)-6-(4-benzyloxy-phenyl)-3-[(R)-1-phenyl-ethyl]-7-oxa-3-aza-bicyclo [4.1.0] heptane.

Example 2

Preparation of the Starting Material a) Preparation of 4-benzyloxybromobenzene 200 g (1.16 mol) of 4-bromophenol was dissolved in 2.1 L of acetone under argon. Then 320 g (2.31 mol) K$_2$CO$_3$ and 3.465 g (23.1 mmol) NaI were added. The mixture was stirred at room temperature and 292.7 g (2.31 mol) of benzyl chloride was added during 1hour. Then the mixture was boiled during 48 h. The acetone (ca. 500 mL) was partially removed on the rotary evaporator. 1.2 L 10% aq. Na$_2$CO$_3$ was added to the residue. After extraction with ethyl acetate (1×1 L+2×500 mL) the organic phase was washed with 1 L of a half-saturated NaCl solution. After drying over Na$_2$SO$_4$ and concentrating, the main part of the benzyl chloride was removed. 400 mL of pentane was added to the residue. The crystallisation began during stirring at 0° C. The crystals were separated and washed with 2×150 mL pentane and dried during 2 h at 15 mbar (40 °C. bath temperature) and 2 h under high vacuum at room temperature to yield 230 g (75%) 4-benzyloxybromobenzene.

b) Preparation of 1-ethyl-1-methyl-4-oxo-piperidinium-iodide 730 mL acetone 124 g (876 mmol) methyl iodide was added to a solution of 93 g (730 mmol) of 1-ethyl-4-piperidone during 30 minutes. The temperature was kept at 25–30° C. The product began to precipitate after addition of ⅓ of the methyl iodide. The mixture was stirred for 5 hours at 22° C. and 30 minutes at 0° C. The cold suspension was filtered and the product was washed with acetone to yield 188 g (95%) 1-ethyl-1-methyl-4-oxo-piperidinium iodide. c)

Preparation of (R)-1-(1-phenyl-ethyl)-piperidin-4-one a) 84.6 g (698 mmol) of (R)-(+)-1-phenylethylamine and 1.4 L ethanol were mixed under argon. A solution of 203 g (1.47 mol) K$_2$CO$_3$ in water was added. The mixture was heated at 80° C. under stirring and a solution of 188 g (698 mmol) 1-ethyl-1-methyl-4-oxo-piperidinium iodide in 700 mL water was added during 1hour. The mixture was heated again for 105 minutes under stirring and then ethanol was removed on the rotary evaporator.

The residue was extracted with dichloromethane (1×1.5 L+1×1 L). The organic phases were washed with half-saturated NaCl solution (2×800 mL) and dried with Na$_2$SO$_4$. After evaporation of the solvent 144 g crude (R)-1-(1-phenyl-ethyl)-piperidin-4-one was obtained. 70mL 37% HCl were added at 5° C. to 300 mL of isopropanol during 30 minutes. The mixture was added during 2 hours under stirring at 15–20° C. to a solution of 144 g crude (R)-1-(1-phenyl-ethyl)-piperidin-4-one in 100 mL ethylacetate. Crystallisation began after addition of ⅓ of the above mixture. The suspension was stirred overnight at room temperature and then for 3 hours at 0° C. After adding 80 mL of pentane the mixture was stirred again for 3 hours at 0° C. The product was separated and washed with isopropanol (3×70 mL). After drying the hydrochloride (188 g) was suspended in 1 L dichloromethane and 700 mL of 10% $Na_2CO_3$ was added. The organic phase was separated and washed with half-saturated NaCl (1×1L). After drying over $MgSO_4$ the organic phase was concentrated. The residue was dried over 2 hours in high vacuum, to yield 113 g (R)-1-(1-phenyl-ethyl)-piperidin-4-one.

d) Preparation of (R)-4-(4-benzyloxy-phenyl)-1-(1-phenyl-ethyl)-piperidin-4-ol 175.2 g (666 mmol) 4-benzyloxybromobenzene was dissolved in 1.4 L dry THF (MS 4 A) under argon. The solution was cooled to −75° C. and a solution of 416 mL 1.6 M butyllithium (666 mmol) in hexane was added during 40 minutes. After stirring for 1 hour a solution of 113 g (555 mmol) (R)-1-(1-phenyl-ethyl)-piperidin-4-one in 400 mL THF was added during 1hour at −75° C. The mixture was stirred for another 1 hour and, after heating to room temperature, poured into 1.5 L of ice-water. The mixture was extracted with 1 L ethyl acetate. The organic phase was washed with 1 L of a half-saturated NaCl solution, dried over $Na_2SO_4$ and concentrated to yield 262 g of (R)-4-(4-benzyloxy-phenyl)-1-(1-phenyl-ethyl)-piperidin-4-ol.

e) Preparation of (R)-4-(4-Benzyloxy-phenyl)- 1-(1-phenyl-ethyl)- 1,2,3.6 tetrahydropyridine 121.7 g crude (R)-4-(4-benzyloxy-phenyl)-1-(1-phenyl-ethyl)-piperidin-4-ol was dissolved at 40° C. in 1.21 L dichloroethane. 59.4 g (471 mmol) of oxalic acid dihydrate (Merck 492) was added. The mixture was boiled for 3 hours, while 20 mL of water was separated. The reaction mixture was washed at room temperature with 1.2 L 10% $Na_2CO_3$. The precipitate (52 g) was separated from filtrate A and added to a mixture of 250 mL 2 N NaOH and 300 mL dichloromethane, where it was dissolved after stirring for 30 minutes at 30–35° C. The organic phase was separated and washed with a half-saturated NaCl solution. The obtained precipitate was separated and dissolved in 200 mL dichloromethane and 60 mL methanol. The combined organic phases were concentrated after drying over $Na_2SO_4$. 80 mL ethyl acetate was added to the residue and stirred for 2 hours. The crystals were separated, washed with pentane, and dried to yield 36.5 g of (R)-4-(4-benzyloxy-phenyl)-1-(1-phenyl-ethyl)-1,2,3,6-tetrahydropyridine was obtained.

The organic phase of the above-mentioned filtrate A was washed with 1.5 L of a half-saturated NaCl solution. After drying the organic phase was concentrated. 80 mL ethylacetate and 30 mL ether were added to the residue. After stirring for 3 hours at 0° C. the crystals were separated and then washed with ethyl acetate (2×20 mL) and pentane (50 mL) and dried to yield 33.0 g of (R)4-(4-benzyloxy-phenyl)-1-(1-phenyl-ethyl)-1,2,3,6-tetrahydropyridine.

In total: 33.0 g +36.5 g =69.5 g (R)-4-(4-benzyloxy-phenyl)-1-(1-phenyl-ethyl)-1,2,3,6-tetrahydropyridine (73% based on (R)-1-(1-phenyl-ethyl)-piperidin-4-on) was obtained.

Example 3

Preparation of starting material
a) Preparation of 1-Isopropenyl-4-benzyloxy-benzene
At room temperature 29.6 g of methyltriphenylphosphonium bromide (83 mmol) was suspended in 75 mL of tetrahydrofuran. A solution of 9.2 g of potassium tert-butoxide (82 mmol) in 35 mL of tetrahydrofuran was added over 30 minutes, and the mixture was stirred for 10 minutes at room temperature and was then cooled to 0° C. At this temperature, a solution of 17.0 g of 4-benzyloxyacetophenone (75 mmol) in 100 mL of tetrahydrofuran was added during 1.5 hours to the solution of the ylide. Stirring at 0° C. was continued for 1 hour, then 11 mL of acetic acid was added to the reaction mixture. The reaction mixture was poured into a mixture of 300 mL of saturated aq. sodium bicarbonate, 200 g of ice and 250 mL of ethyl acetate. Then the aqueous phase was extracted with ethyl acetate. The organic phases were washed with 200 mL of 20% aq. sodium chloride, combined, dried ($Na_2SO_4$) and evaporated under reduced pressure to give 40.5 g of a white solid residue. The residue was suspended in 250 mL of hexane, and the mixture was stirred overnight at room temperature. The tripenylphosphinoxide was filtered off and washed with hexane. The filtrate was evaporated to give 15.8 g of a white solid. In order to remove traces of triphenylphosphine oxide, the product was passed through a pad of silica gel using hexane-ethyl acetate 95:5 (750 mL) as eluent. The combined fractions containing the desired compound were evaporated. The residue was suspended in 80 mL of pentane, then the product was collected by filtration, washed with pentane and dried to a constant weight to yield 14.1g 1-isopropenyl-4-benzyloxy-benzene.

b) Preparation of (R)-4-(4-benzyloxy-phenyl)-1-(1-phenyl-ethyl)-1,2,3,6-tetrahydro-pyridine At room temperature 20.7 g of (R)-1-phenylethylamine hydrochloride (131 mmol) was dissolved in 60 mL of water. 22 mL of 36.5% aqueous formaldehyde was added and the mixture was stirred 10 minutes at room temperature and then warmed up to 40° C. At this temperature, a solution of 26.75 g of 1-isopropenyl-4-benzyloxy-benzene (119 mmol) in a mixture of 30 mL of dioxane and 74 mL of dichloromethane was continuously added over 1.25 hours. During and after the addition of the olefin solution, dichloromethane was distilled off. After the removal of dichloromethane, the reaction mixture was stirred at 70° C. overnight. A solution of 9.96 g of conc. sulphuric acid (99 mmol) in 30 mL of water was added during 5 minutes to the reaction mixture which was then heated to 95–100° C. and stirred at this temperature for 5.5 hours. The reaction mixture was slowly poured into a mixture of 250 mL of 10% aq. sodium carbonate and ice and then extracted with 600 mL of dichloromethane. The organic phases were extracted with one portion of 600 mL of 20% aq. sodium chloride, combined, dried ($Na_2SO_4$) and evaporated under reduced pressure to give 64 g crude product as a brown-red oil which partially crystallised. The crude product was dissolved in 250 mL of dichloromethane. 120 mL of isopropanol was added and the dichloromethane as well as a small part of the isopropanol was distilled off at reduced pressure (rotary evaporator, bath 45° C.). White crystals started to precipitate, and the suspension was stirred at 0° C. for 2 hours. The crystals were collected on a filter funnel and washed with three portions of 50 mL of cold isopropanol and with 60 mL of hexane. After drying for 2 hours at 16 mbar50° C. and for 2 hours at 0.2 mbar/22° C., 29.2 g (66%) (R)-4-(4-benzyloxy-phenyl)-1-(1-phenyl-ethyl)-1,2,3,6-tetrahydro-pyridine was obtained.

Example 4

Preparation of Starting Material
a) Preparation of 2-(4-benzyloxy-phenyl)-propan-2-ol
The reaction flask was charged under argon with 3.45 g of magnesium (142 mmol). A solution of 21.16 g of methyl iodide (147 mmol) in 120 mL of tert-butyl-methyl-ether was added during 45 minutes at 45° C. under stirring. Then stirring was continued for 1 hour at 45° C. and then a solution of 27.12 g of 4-benzyloxyacetophenone (120 mmol) in 100 mL of tetrahydrofuran was added during 45 minutes, while a temperature of 45° C. was again maintained. Stirring at 45° C. was continued for 1.5 hours. After cooling to room temperature, the white suspension was poured into a mixture of 100 mL of 10% aqueous ammonium chloride and of ice and extracted with 150 mL of ethyl acetate. The aqueous phase was separated and extracted with 100 mL of ethyl acetate. The organic phase was washed with 120 mL of 20% aq. sodium chloride, combined, dried (MgSO$_4$) and evaporated under reduced pressure to give 29.9 g of crude product as an oil which partially crystallised. The crude product was taken up in 30 mL of dichloromethane. The solution was concentrated at the rotary evaporator almost to dryness. Then 6 mL of ethyl acetate was added followed by gradual addition of a total of 180 mL of hexane. The suspension was then kept at 0° C. for 30 minutes. The crystals were collected and washed with cold hexane. After drying for 2 hours at 16 mbar/45° C., 26.7 g (92%) 2-(4-benzyloxy-phenyl)-propan-2-ol was obtained.

b) Preparation of (R)4-(4-benzylox -phenyl)-1-(1-phenyl-ethyl)-1,2,3,6-tetrahydro-pyridine At room temperature 6.94 g of (R)-1-phenylethylamine hydrochloride (44 mmol) was dissolved in 24 mL of water. 8.0 g of 36.5% aqueous formaldehyde (2.92 g HCHO, 97 mmol) was added and the mixture was stirred for 10 minutes. Then, a solution of 9.68 g of 2-(4-benzyloxy-phenyl)-propan-2-ol (40 mmol) in 10 mL of dioxane was added. The reaction mixture was heated to 70° C. and stirred overnight at this temperature. A solution of 1.72 g of conc. sulphuric acid (17.6 mmol) in 8 mL of water was added to the reaction mixture within 5 minutes. Then the mixture was heated to 100° C. and stirred at this temperature for 7 hours. The reaction mixture was slowly poured into a mixture of 150 mL of 10% aq. sodium carbonate and 50 g of ice and extracted with 450 mL of dichloromethane. The organic phases were extracted with 150 mL of water, combined, dried (Na$_2$SO$_4$) and evaporated under reduced pressure to give 18.1 g crude product as a orange-red oil which partially crystallised.

The crude product was dissolved in 60 mL of dichloromethane. 80 mL of isopropanol was added and the dichloromethane as well as a small part of the isopropanol was distilled off at 400 mbar (rotary evaporator, bath 55° C.). White crystals precipitated, and the suspension was stirred 1 hour at room temperature and additionally 1 hour at 5° C. The crystals were collected and washed with 2 portions of 25 mL isopropanol and with 2 portions of 25 mL hexane. The product was then dried for 2 h at 16 mbar/40° C. and for 3 h at 0.2 mbar/22° C. to yield 9.1 g (61%) of (R)-4-(4-benzyloxy-phenyl)-1-(1-phenyl-ethyl)-1,2,3,6-tetrahydro-pyridine.

c) Preparation of R)-1-phenylethylamin hydrochloride

At room temperature 122 g of (R)-1-phenylethylarnine (1.0 mol) was dissolved in 30 mL of isopropanol. The solution was stirred and cooled to 0° C. Then, a previously prepared solution of 100 mL of 37% hydrochloric acid (118 g, 1.2 mol) in 320 mL of isopropanol was added during 1 hour. The solution was stirred at 0° C. for an additional 40 minutes, and then it was concentrated on a rotary evaporator (16 mbar, bath 45° C.) to a volume of 300 mL. The translucent gel which had formed was transferred into a 1.5 l flask, then, under stirring, 250 mL of tert-butyl-methyl-ether was slowly added. Crystals started to form and the suspension was stirred at 0° C. for 3 hours. The product was collected by filtration, washed with 100 mL of tert-butyl-methyl-ether and dried at 30° C./16 mbar for 4 hours to yield 133 g (84%) of 1-phenylethylamine hydrochloride.

Example 5

Preparation of Starting Material a) Preparation of methyl 4-benzyloxybenzoate

To a solution of 15.2 g of methyl4-hydroxybenzoate (100 mmol) in 125 mL of N,N-dimethylformamide was added under stirring 33.13 g of potassium carbonate (240 mmol). Then 17.45 g of benzyl bromide (102 mmol) was added within 5 minutes. The mixture was stirred at 25° C. using a water bath. The reaction was complete after 3 hours. The reaction mixture was poured into a mixture of 180 g of ice and 200 mL of ethyl acetate. After extraction, the aqueous phase was separated and extracted with three portions of 80 mL of ethyl acetate. The organic phase was washed with two portions of 150 mL of water, combined, dried (MgSO$_4$) and partially concentrated to give a thick suspension. 60 mL of pentane was added and the suspension was stirred during 2 hours at room temperature. The crystalline methyl 4-benzyloxybenzoate was collected on a filter, washed with pentane and dried.

b) Preparation of 2-(4-benzyloxy-phenyl)-propan-2-ol

Under argon 6.63 g of magnesium (273 mmol) was suspended in 15 mL of tert-butyl methyl ether. A solution of 38.68 g of methyl iodide (273 mmol) in 145 mL of tert-butyl methyl ether was added during 45 minutes under stirring while maintaining the temperature at 40° C. Then stirring was continued at 40° C. for 1.5 hours and then the mixture was cooled to room temperature. A solution of 30.0 g of methyl 4-benzyloxybenzoate (124 mmol) in 120 mL of tetrahydrofuran was then added during 1 hour. The temperature was kept at 20° C. After complete addition, the reaction mixture was heated to 42° C. and stirred 3 hours at this temperature. After cooling to room temperature, the reaction mixture was poured into a mixture of 300 mL of 10% aqueous ammonium chloride and 100 g of ice and extracted with ethyl acetate. The organic phases were washed with water and saturated aqueous sodium bicarbonate, combined, dried and evaporated to give the crude product as an oil which partially crystallised. The product was dissolved at 25° C. in diethyl ether. When crystals started to separate the solution was cooled to 18° C. After 30 minutes hexane was added. The suspension was then stirred for 1 hour at 5° C. The crystalline 2-(4-benzyloxy-phenyl)-propan-2-ol was collected on a filter and washed with hexane.

c) Preparation of (R)-4-(4-benzyloxy-phenyl)-1-(1-phenyl-ethyl)-1,2,3,6-tetrahydro-pyridine At room temperature, the reaction flask was charged with 10.66 g of (R)-1-phenylethylamine (88 mmol) and 40 mL of water. Under stirring, the pH of the mixture was adjusted to a value of 4.1 by slow addition of aqueous hydrochloric acid. Then 16.0 g of 36.5% aqueous formaldehyde (5.84 g HCHO, 194 mmol) was added and the mixture was stirred for 10 minutes. A solution of 19.38 g of 2-(4-benzyloxy-phenyl)-propan-2-ol (80 mmol in 20 mL of dioxane) was then added. The reaction mixture was heated to 70° C. and stirred overnight at this temperature. A solution of 3.44 g of conc. sulphuric acid (35 mmol) in 16 mL of water was added during 5 minutes to the reaction mixture which was then heated to 100° C. and stirred at this temperature for 7 hours. The reaction mixture was slowly poured into a mixture of 300 mL of 10% aq. sodium carbonate and 100 g of ice and extracted with dichloromethane. The organic phases were extracted with water, combined, dried and evaporated to an orange-red oil which partially crystallised. The crude product was dissolved in 120 mL of dichloromethane. 160 mL of isopropanol was added and the dichloromethane as well as a part of the isopropanol was distilled off at 400 mbar (rotary evaporator, bath 55° C.). White crystals precipitated. The crystals were collected on a filter funnel and washed with isopropanol and then with hexane. The obtained (R)-4-(4-benzyloxy-phenyl)-1-(1-phenyl-ethyl)-1,2,3,6-tetrahydro-pyridine was then dried for 2 h at 16 mbar/40° C. and for 3 h at 0.2 mbar/22° C.

Example 6

Preparation of a precursor for renin inhibitors

Preparation of (3S)4-(4-benzyloxy-phenyl)-1-[(1R)-phenyl-ethyl]-1,2,3,6-tetrahydro-pyridin-3-ol 5.77 g of (1R, 6R)-6-(4-benzyloxy-phenyl)-3-[(R)-1-phenyl-ethyl]-7-oxa-3-aza-bicyclo [4.1.0] heptane (15 mmol) and 225 mL of tert-butyl methyl ether were charged under argon in the reaction vessel. The mixture was cooled under stirring to −15° C. and, at this temperature, 18.75 mL of 1.6M phenyllithium (30 mmol) was continuously added over 45 min from a syringe pump via a teflon cannula. Stirring was continued for a 3.5 hours. At this point the reaction was complete. The light brown reaction mixture was poured onto a mixture of 100 mL of 7% aqueous sodium bicarbonate and of ice and extracted with 250 mL of ethyl acetate. The aqueous phase was separated and extracted with a fresh portion of 250 ml of ethyl acetate. The organic phases were washed with two portions of 100 mL i.e. 200 mL of 20% aq. sodium chloride, combined, dried ($MgSO_4$) and evaporated under reduced pressure to give 6.8 g crude product as a brown solid. The crude product was taken up in 30 mL of dichloromethane. The solution was concentrated at the rotary evaporator to an oil of approx. 9 g weight. 10 mL of ethyl acetate was added and crystals started to separate. A second portion of 5 mL of ethyl acetate was added followed by approx. 25 mL of hexane. The suspension was then stirred at 0° C. for 2 hours. The crystals were collected and washed with a portion of cold hexane. The product was dried for 2 hours at 16 mbar/45° C. to give 5.0 g (86%) of (3S)-4-(4-benzyloxy-phenyl)-1-[( 1R)-phenyl-ethyl]-1,2,3,6-tetrahydro-pyridin-3-ol as light brown crystals, m.p. 112–114° C.

Example 7

Preparation of Renin Inhibitor

Preparation of (3R,4S,5S)-4-14-(3-benzyloxy-propoxy)-phenl]-5-ethoxy-3-(naphthalen-2-ylmethoxy)-piperidine a) 49.3 g (128 mmol) of (3S)-4-(4-benzyloxy-phenyl)-1-[(1R)-phenyl-ethyl]-1,2,3,6-tetrahydro-pyridin-3-ol were dissolved in 250 ml of N,N-dimethylformamide, treated portionwise with 25 g (about 600 mmol) of sodium hydride dispersion in refined oil (55–65%) and the reaction mixture was heated to 50° C. under argon for 1 hour. After cooling to 5° C. the mixture was treated slowly with 23 ml (285 mmol) of ethyl iodide and stirred without cooling for one hour. Thereupon, the reaction mixture was poured into 2 liters of ice-water and extracted three times with 1 liter of ethyl acetate. The combined ethyl acetate phases were subsequently washed with water, dried over magnesium sulfate and evaporated on a rotary evaporator at a maximum 40° C. The resulting residue was chromatographed on silica gel with hexane/ethyl acetate to yield (3S)-4-(4-benzyloxy-phenyl)-3-ethoxy-1-[(1R)-phenyl-ethyl]-1,2,3,6-tetrahydro-pyridine as a colorless oil.

b) 35 g (84.6 mmol) of (3S)-4-(4-benzyloxy-phenyl)-3-ethoxy-1-[(1R)-phenyl-ethyl]-1,2,3,6-tetrahydro-pyridine were dissolved in 500 ml of 1,2-dimethoxyethane, treated with 9.91 g (262 mmol) of sodium borohydride and then treated while cooling at a maximum 28° C. with a solution of 44.3 ml (353 mmol) of boron trifluoride etherate in 44.3 ml of 1,2-dimethoxyethane and the reaction mixture was stirred at room temperature for 2 hours. Subsequently, while cooling at a maximum of 35° C., 169 ml of 4.1N potassium hydroxide solution followed by 33.9 ml of 30% hydrogen peroxide solution were added dropwise and the reaction mixture was heated under reflux for 3 hours. After cooling to room temperature the reaction solution was poured into 2 liters of water and extracted twice with 1 liter of dichloromethane each time. The combined dichloromethane phases were washed with water, dried over magnesium sulphate and evaporated on a rotary evaporator at a maximum 40° C. The resulting residue was chromatographed on silica gel with hexane/ethyl acetate to yield (3R,4R,5S)-(4-benzyloxy-phenyl)-5-ethoxy-1-[(1R)-phenyl-ethyl]-piperidin-3-ol) as a colorless oil.

c) 20 g (46.3 mmol) (3R,4R,5S)-(4-benzyloxy-phenyl)-5-ethoxy-1-[(1R)-phenyl-ethyl]-piperidin-3-ol dissolved in 500 ml methanol were hydrogenated in the presence of 3.5 g of palladium catalyst (10% on charcoal) for 7 hours. The reaction mixture was then filtered and evaporated yielding crude (3R,4R,5S)-5-ethoxy-4-(4-hydroxy-phenyl)-piperidin-3-ol MS: 237(M+).

d) 11 g (46.3 mmol) crude (3R,4R,5S)-5-ethoxy-4-(4-hydroxy-phenyl)-piperidin-3-ol were dissolved in 100 ml dioxane/50 ml water and treated with 11 g (50 mmol) di-tert-butyldicarbonate and 8.4 g (100 mmol) sodium hydrogencarbonate. The reaction mixture was then stirred for 2 hours. 100 ml 2 N NaOH were then added and the mixture again stirred for an additional hour. It was then acidified with solid citric acid. Then, the resulting product was extracted 3 times with dichloromethane, the organic phases were washed twice with distilled water, then dried over magnesium sulphate, filtered and concentrated in a water-jet vacuum. The resulting crude product was chromatographed on silica gel with dichloromethanelethyl acetate to yield (3R,4R,5S)-5-ethoxy-3-hydroxy-4-(4-hydroxy-phenyl)-piperidine-1-carboxylic acid tert-butylester as colorless oil; MS: 338 (M+H$^+$).

e) A solution of 11.8 g (35.0 mmol) of (3R,4R,5S)-5-ethoxy-3-hydroxy-4-(4-hydroxy-phenyl)-piperidine-1-carboxylic acid tert-butylester in 40 ml of dimethylformamide was treated in succession with 10.3 g (45.0 mmol) of 3-bromo-propoxymethyl-benzene and 8.29 g (60.0 mmol) of potassium carbonate. This mixture was stirred at 120° C. for 26 hours. Subsequently, it was filtered, concentrated to a few milliliters, poured into 300 ml of an ice/water mixture and extracted three times with 100 ml of dichloromethane each time. The combined organic phases were washed once with a small amount of water, dried over magnesium sulphate, evaporated under reduced pressure and dried in a high vacuum. The resulting crude product was separated on silica gel using a mixture of dichloromethane and methanol as the eluent and yielded (3R,4R,5S)-4-[4-(3-benzyloxy-propoxy)-phenyl]-5-ethoxy-3-hydroxy-piperidine-1-carboxylic acid tert-butylester as colorless oil; MS: 486 (M+H$^+$); 508 (M+Na$^+$).

f) 14.6 g (30.0 mmol) of (3R,4R,5S)-4-[4-(3-benzyloxy-propoxy)-phenyl]-5-ethoxy-3-hydroxy-piperidine-1-carboxylic acid tert-butylester and 7.74 g (35.0 mmol) of 2-bromomethyl-naphthalene were dissolved in 110 ml of dimethylformamide under argon and then 1.77 g (40.0 mmol) of sodium hydride dispersion (55% in mineral oil) was added. Subsequently, the mixture was stirred at room temperature for 5 hours. The reaction mixture was poured onto ice-water, the resulting product was extracted 3 times with dichloromethane, the organic phases were washed twice with distilled water, then dried over magnesium sulfate, filtered and concentrated in a water-jet vacuum. The resulting crude product was chromatographed on silica gel with dichloromethane and methanol to yield (3R,4S,5S)-4-[4-(3-benzyloxy-propoxy)-phenyl]-5-ethoxy-3-(naphthalen-2-ylmethoxy)-piperidine-1-carboxylic acid tert-butylester as colorless oil; MS: 626.5(M+H$^+$).

g) 14.4 g (23.0 mmol) of (3R,4S,5S)-4-[4-(3-benzyloxy-propoxy)-phenyl]-5-ethoxy-3-(naphthalen-2-ylmethoxy)-piperidine-1-carboxylic acid tert-butylester were placed in 350 ml of abs. methanol at 0° C., then 24 ml (48 mmol) of hydrochloric acid in methanol (2.0 molar) were added dropwise at 5° C. max. and thereafter the mixture was warmed to room temperature. After 120 minutes the reaction mixture was poured into ice-cold sodium hydrogen carbonate solution and the product was extracted three times with dichloromethane, the organic phases were washed once with distilled water, then dried over magnesium sulphate, filtered and concentrated in a water-jet vacuum. The resulting crude product was chromatographed on silica gel with dichloromethane and methanol to yield (3R,4S,5S)-4-[4-(3-benzyloxy-propoxy)-phenyl]-5-ethoxy-3-(naphthalen-2-ylmethoxy)-piperidine as colorless oil; MS: 526(M+H$^+$).

What is claimed is:

1. A compound having the formula

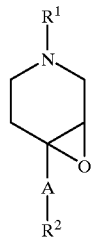

1 wherein

A is arylene;
R$^1$ is —C*R$^3$R$^4$R$^5$;
R$^2$ is —O-alkyl, —O-cycloalkyl, —O-alkenyl, —O-aryl, —O-aralkyl, —O-aralkoxyalkyl, —O-alkylsulfonyl, —O-arylsulfonyl, chlorine, bromine or iodine;
R$^3$ is hydrogen;
R$^4$ is aryl;
R$^5$ is alkyl, cycloalkyl, aryl, alkoxyalkyl or hydroxyalkyl; and
C* is an asymmetric carbon atom; and
salts of said compound.

2. The compound of claim 1, wherein R$^5$ is alkyl or cycloalkyl.

3. The compound of claim 1, wherein R$^4$ is phenyl which is unsubstituted or substituted by one or more groups independently selected from the groups consisting of alky, halogen and nitro.

4. The compound of claim 1, wherein R$^4$ is phenyl and R$^5$ is methyl.

5. The compound of claim 1, wherein A is phenylene which is unsubstituted or substituted by one to four substituents independently selected from the group consisting of alky, halogen and nitro.

6. The compound of claim 1, wherein R$^2$ is selected from the group consisting of —O-benzyl and —O-methyl.

7. The compound of claim 1, (1R, 6R)-6-(4-benzyloxyphenyl)-3-[(R)-1-phenyl-ethyl]-7-oxa-3-aza-bicyclo[4.1.0] heptane.

8. The compound of claim 1, (1S, 6S)-6-(4-benzyloxyphenyl)-3-[(R)-1-phenyl-ethyl]-7-oxa-3-aza-bicyclo[4. 1.0] heptane.

9. A process for the preparation of a compound of formula 1, or a salt thereof,

1 comprising:
epoxidation of a compound of formula 2, or a salt thereof,

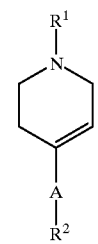

2 wherein

| | |
|---|---|
| A | is arylene; |
| R$^1$ | is -C*R$^3$R$^4$R$^5$; |
| R$^2$ | is -O-alkyl, -O-cycloalkyl, -O-alkenyl, -O-aryl, -O-aralkyl, -O-aralkoxyalkyl, -O-alkylsulfonyl, -O-arylsulfonyl, chlorine, bromine or iodine; |
| R$^3$ | is hydrogen; |
| R$^4$ | is aryl; |
| R$^5$ | is alkyl, cycloalkyl, aryl, alkoxyalkyl or hydroxyalkyl; and |
| C* | is an asymmetric carbon atom. |

10. The process of claim 9 further comprising the step of isolating a desired stereoisomer.

11. The process of claim 10, wherein the desired stereoisomer is isolated by crystallisation of a compound of formula 1 of a salt thereof.

12. The process of claim 11, followed by reacting with a metal alcoholate, a lithium amide or an organolithium compound.

13. The process of claim 12, wherein the metal alcoholate is potassium t-butoxide, aluminum isopropoxide, or titanium (IV) t-butoxide.

14. The process of claim 13, wherein the organolithium compound is phenyllithium.

15. The process of claim 9, wherein R$^5$ is alkyl or cycloalkyl.

16. The process of claim 9, wherein R$^4$ is phenyl which is unsubstituted or substituted by one or more groups independently selected from alkyl, halogen or nitro.

17. The process of claim 9, wherein $R^4$ is phenyl and $R^5$ is methyl.

18. The process of claim 9, wherein A is phenylene which is unsubstituted or substituted by one to four substituents each of which is independently selected from the group consisting of alkyl, halogen and nitro.

19. The process of claim 9, wherein R is —O-benzyl or —O-methyl.

20. The process of claim 9, wherein a compound of formula 2 is reacted with a halogen or a halogen delivering agent.

21. The process of claim 20, wherein the halogen is bromine.

* * * * *